United States Patent [19]
Little

[11] Patent Number: 5,313,957
[45] Date of Patent: * May 24, 1994

[54] GUIDE WIRE MOUNTED PRESSURE TRANSDUCER

[75] Inventor: Richard L. Little, New Hope, Minn.

[73] Assignee: MedAmicus, Inc., Minneapolis, Minn.

[*] Notice: The portion of the term of this patent subsequent to Apr. 9, 2008 has been disclaimed.

[21] Appl. No.: 682,661

[22] Filed: Apr. 8, 1991

Related U.S. Application Data

[63] Continuation-in-part of Ser. No. 461,178, Jan. 5, 1990, Pat. No. 5,005,584.

[51] Int. Cl.⁵ ............... A61B 5/00; A61B 5/02; A61M 25/00; G01L 7/08
[52] U.S. Cl. .................... 128/748; 128/667; 128/675; 664/287; 73/748
[58] Field of Search .............. 128/637, 665-667, 128/672-675, 772, 748, 634, 664; 73/705, 708, 715; 664/287

[56] References Cited

U.S. PATENT DOCUMENTS

| | | |
|---|---|---|
| 3,273,447 | 9/1966 | Frank . |
| 3,686,958 | 8/1972 | Porter et al. . |
| 4,020,829 | 5/1977 | Wilson et al. . |
| 4,201,222 | 5/1980 | Haase . |
| 4,210,029 | 7/1980 | Porter . |
| 4,487,206 | 12/1984 | Aagard . |
| 4,543,961 | 10/1985 | Brown . |
| 4,593,701 | 6/1986 | Kobayashi et al. . |
| 4,599,901 | 7/1986 | Hirschfeld . |
| 4,611,600 | 9/1986 | Cohen . |
| 4,676,249 | 6/1987 | Arenas et al. . |
| 4,711,246 | 12/1987 | Alderson . |
| 4,712,566 | 12/1987 | Hok . |
| 4,722,348 | 2/1988 | Ligtenberg et al. ........... 128/748 |
| 4,737,153 | 4/1988 | Shimamura et al. . |
| 4,787,396 | 11/1988 | Pidorenko . |
| 4,805,630 | 2/1989 | Storey ........................ 128/675 |
| 4,924,870 | 5/1990 | Wlodarczyk et al. . |
| 4,924,877 | 5/1990 | Brooks ........................ 128/748 |
| 4,936,310 | 6/1990 | Engstrom et al. . |
| 4,941,473 | 7/1990 | Tenerz et al. . |
| 4,953,553 | 9/1990 | Tremulis . |
| 4,991,590 | 2/1991 | Shi ............................. 128/667 |
| 5,005,584 | 4/1991 | Little .......................... 128/748 |
| 5,018,529 | 5/1991 | Tenerz et al. ................. 128/667 |
| 5,067,491 | 11/1991 | Taylor III et al. ............ 128/748 |
| 5,080,297 | 9/1991 | Metzger ...................... 128/675 |
| 5,085,223 | 2/1992 | Lars et al. ................... 128/675 |

OTHER PUBLICATIONS

Copy of materials from Cardiovascular Procedures, Tilkian et al., Copyright 1986, pp. 3-23, 36.
One page sheet entitled *Catheter Introducer/Kit/Tray*, printed on behalf of Argon Medical Corporation, Copyright 1985.

Primary Examiner—Randall L. Green
Assistant Examiner—K. Reichle
Attorney, Agent, or Firm—Moore & Hansen

[57] ABSTRACT

A physiological pressure transducer assembly mounted on a transvenously-insertable guide wire is disclosed. The multiple coils of the guide wire define an elongated tubular passage within which fiber optic leads are contained for the transmission of light signals to a pressure transducer. A window or aperture is cut along a restricted portion of the length of the guide wire coil to provide a pressure-sensing aperture over which an elastic, pressure-sensitive membrane is positioned. The coils of the guide wire adjacent to the sensing aperture are joined together for increased rigidity along the length of the pressure transducer assembly, as by soldering or brazing. A separate, cylindrical housing, preferably of molded plastic, is wholly contained within the reinforced length of the guide wire. The proximal end portions of fiber optic sending and receiving leads or paths are received and contained within the housing in a predetermined arrangement and geometry defining a light-transmitting gap. Light transmission across the gap is controllably attenuated by deflection of the pressure-responsive membrane in response to pressure changes within a person's body, and the attenuated light signals are transmitted to an external control unit as indicative of pressure changes. A reflector positioned on an end cap closing the proximal end of the elongated guide wire is utilized to reflect signals from the signal transmitting, fiber optic lead or path to the proximal end portion of a return signal, fiber optic lead or path.

20 Claims, 1 Drawing Sheet

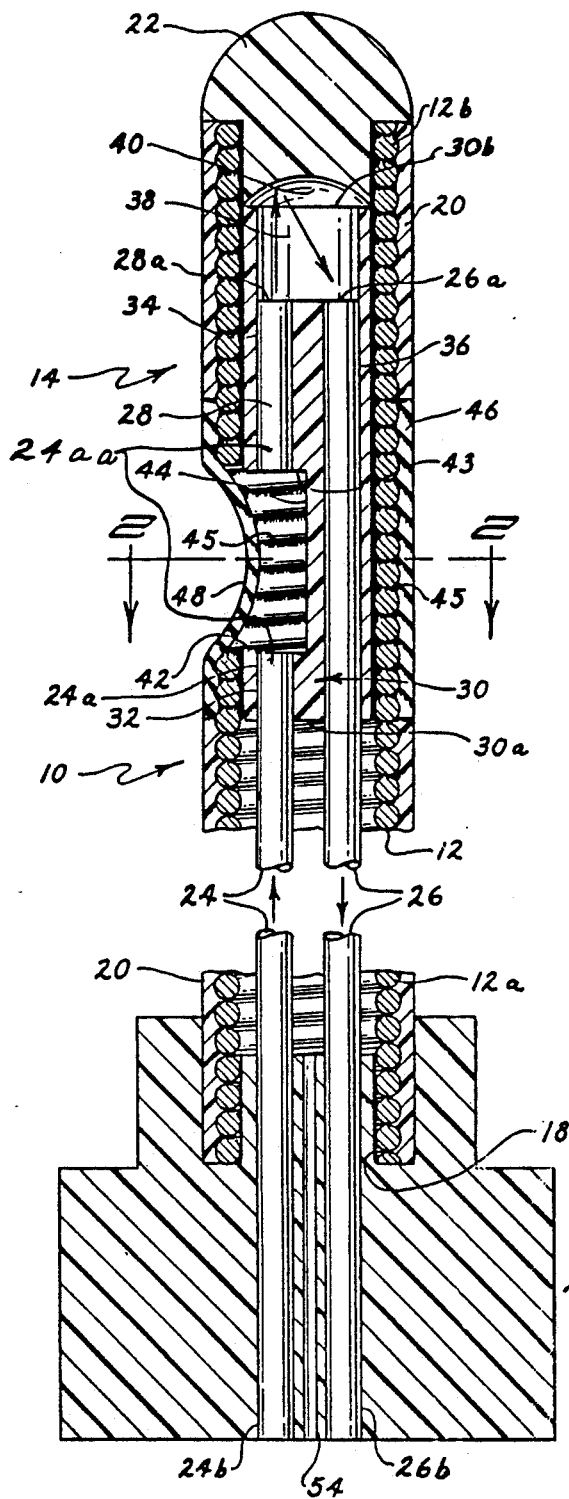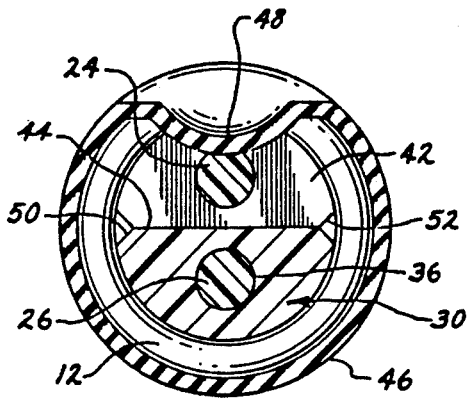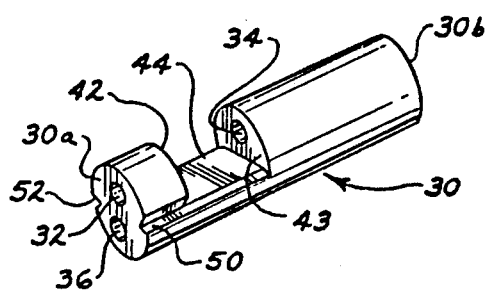

GUIDE WIRE MOUNTED PRESSURE TRANSDUCER

BACKGROUND OF THE INVENTION

This application is a continuation-in-part of applicant's copending application Ser. No. 07/461,178 filed Jan. 5, 1990 entitled FIBER OPTIC PRESSURE TRANSDUCER, which will issue as U.S. Pat. No. 5,005,584 on Apr. 9, 1991.

This invention is directed to a pressure transducer, and in particular to a fiber optic pressure transducer mounted on a medical guide wire for intravenous insertion.

Miniature, fiber optic coupled pressure transducers of the aforesaid type have been mounted on catheters in various structural arrangements for physiological pressure measurements within the vascular system of a patient. See, for example, U.S. Pat. No. 4,787,396 to Pidorenko and U.S. Pat. No. 4,611,600 to Donald M. Cohen. Such prior art devices suffer from various shortcomings, including the mounting arrangement of a pressure transducer assembly on a catheter device or on fiber optic leads in cumbersome structures which require a pressure transducer assembly several times greater in diameter than the overall diameter of the fiber optic leads utilized to transmit light from a light-generating source. Such prior art pressure transducers have utilized pressure sensitive diaphragms or membranes mounted on a transducer head to detect changes in pressure within a patient's vascular system. The flexible diaphragm or membrane deflects in response to such internal body pressure changes to move in a manner interrupting or attenuating the transmission of light through one or more fiber optic leads, with the change in light transmission serving as a calibrated signal indicative of a pressure change. The aforesaid patent to Cohen, as well as U.S. Pat. No. 3,273,447 to Frank, disclose the use of a mirror or reflector in the pressure transducer head to reflect light transmitted through one or more fiber optic leads, the reflection of light being interrupted or attenuated by deflection of the flexible membrane or diaphragm in response to pressure changes within a person's vascular system.

The above-referenced copending patent application of Applicant discloses an improved fiber optic pressure transducer for intravascular applications wherein the fiber optic pressure transducer assembly is mounted on a coiled guide wire of the type used for insertion of catheters intravenously. That guide wire and fiber optic pressure transducer assembly has the particular advantage of greatly reducing the size of the pressure transducer assembly and facilitates the insertion of the device intravenously. Guide wires and introducers are normally used as a means for inserting catheters into a patient's vascular system. A guide wire of the type utilized for such purposes is disclosed in U.S. Pat. No. 4,676,249 issued to Arenas et al. It is common cardiovascular practice to pass small diameter guide wires into the central arterial system for the purpose of providing a path over which an angiographic catheter is subsequently introduced to a desired application point. By mounting the fiber optic pressure transducer on such a guide wire, the physician is able to take pressure measurements in the central arterial system using techniques with which the physician is already familiar. This also eliminates the need for passing an additional guide wire through the arterial system for the subsequent introduction of catheters utilized for other purposes, such as an angiographic catheter.

The pressure transducer disclosed herein presents further improvements with respect to facilitating the mounting and reducing the cost of a guide wire mounted, fiber optic pressure transducer assembly.

BRIEF SUMMARY OF THE INVENTION

A primary objective of the present invention is to provide a transvenously insertable guide wire and physiological pressure transducer assembly of the fiber optic type wherein a pressure transducer assembly is mounted on the guide wire in such a way as to significantly minimize the size and cost of the pressure transducer structure, as well as to facilitate the construction and mounting thereof on a guide wire.

A further object is to provide a guide wire mounted, fiber optic pressure transducer of the aforesaid type and construction wherein a pressure-sensitive membrane positioned on the outside of the guide wire is the only element of the pressure transducer assembly which is outside of the guide wire, all of the remaining elements of the pressure transducer being contained within the guide wire.

The aforesaid objectives are realized by joining together the coils of an elongated guide wire comprised of multiple coils defining an elongated tubular passage, along a restricted portion of the length thereof to add rigidity to the guide wire coil along that length, and cutting an opening or window along that portion of the length of the guide wire coil. An elastic, flexible membrane is placed on the outside of the guide wire in covering relation to the opening in the guide wire, with the portion of the membrane covering the opening comprising a pressure-responsive segment exposed to pressure exterior of the guide wire on its outer surface and to pressure inside of the guide wire on its inner surface. The coils of the guide wire are joined together as by brazing or soldering, and also serve to contain a housing within which the proximal end portions of fiber optic light transmission means extending longitudinally within the guide wire are received and contained. Those proximal end portions of the fiber optic light transmission means has a gap along the light transmission path, and the pressure responsive segment of the flexible membrane deflects transversely across that path in response to pressure changes exterior of the membrane outer surface. In this way, light transmission through the fiber optic light transmission means is attenuated to provide light signals calibrated to indicate changes in pressure within a person's vascular system.

A further beneficial aspect of the improved pressure transducer assembly resides in the use of a double path light transmission means comprising two fiber optic leads or paths extending through the guide wire. One of the fiber optic leads is connected to a source of light, and the other fiber optic lead serves to return the light signals transmitted by the first lead to a pressure transducer. The first, light-transmitting lead is advantageously comprised of two segments at its proximal end portion within the aforesaid housing of a pressure transducer assembly. The first lead thus has a terminal end segment on one side of the aforesaid gap in the light transmission means, and a separate, proximal end segment thereof on the opposite side of the gap, so that movement of the pressure-responsive segment of the flexible membrane changes light transmission across the gap between the terminal end segment and the proximal end segment of the first fiber optic path. The gap distance thus can be closely controlled and calibrated by the spacing of the separate, proximal end segment of the first fiber optic lead from its terminal end segment.

As a further advantageous feature of the double fiber optic path construction, the proximal end portions of the two fiber optic paths are optically coupled to each other by means of a reflector spaced apart from those proximal end portions a predetermined distance in opposing relation thereto, so that light signals from the proximal end portion of the first, light-transmitting fiber optic path will be reflected back to the proximal end portion of the second, return signal, fiber optic path. The reflector is preferably a concave, reflective surface formed on or applied to an end cap affixed to the proximal end of the elongated guide wire coil adjacent to the aforesaid housing of the pressure transducer assembly.

The pressure transducer device is also advantageously constructed so as to be able to sense either pressure increases or pressure decreases within the body of a patient. To that end, the aforesaid flexible membrane is made of elastomeric material which is stretched over the opening in the guide wire so as to be in tension when assembled. Thus assembled, the pressure responsive segment of the flexible membrane will be deflected inwardly through the opening in the guide wire into the aforesaid gap in the fiber optic light transmission means proximal end portions. The pressure responsive segment of the membrane will thus present an initial, minimal obstruction to the passage of light across the gap, and a decrease in pressure exterior of the pressure transducer assembly will cause the pressure responsive segment of the membrane to deflect outwardly and thus permit less of an obstruction and greater light transmission across the gap.

These and other objects and advantages of the invention will become readily apparent as the following description is read in conjunction with the accompanying drawings wherein like reference numerals have been utilized to designate like elements throughout the several views.

BRIEF DESCRIPTION OF THE DRAWINGS

FIG. 1 is a longitudinal section view of the guide wire and pressure transducer assembly;

FIG. 2 is a transverse section view of the pressure transducer assembly portion of the device taken along lines 2—2 of FIG. 1; and FIG. 3 is a perspective view of the housing for the pressure transducer assembly.

DESCRIPTION OF THE PREFERRED EMBODIMENT

With reference now to the drawings, the fiber optic pressure transducer and guide wire assembly is generally indicated by reference numeral 10 in FIG. 1. That assembly is comprised of an elongated guide wire indicated by reference numeral 12 and a transducer assembly generally designated by reference numeral 14. The device further includes a connector head 16 having an annular recess 18 in its upper end within which the distal end 12a of the guide wire is received and held.

Guide wire 12 comprises a helically wound metal coil having multiple coils of wire defining an elongated tubular passage. The guide wire is sufficiently flexible to permit it to traverse a patient's vascular system. The proximal end of guide wire 12 is generally indicated by reference numeral 12b. The entire length of guide wire 12 is preferably covered with a seal coating 20. Such a coating is preferably silicone rubber or polyurethane and forms a relatively gas-tight, continuous imperforate barrier to maintain any pressure differential sensed between the interior and exterior surfaces of transducer assembly 10. Coating 20 is shown on the outside of guide wire 12. However, such a coating could also be applied to the inside surface of the guide wire, or to both the inside and outside surfaces. The proximal end 12b of guide wire 12 is closed by an end cap 22, which may be made of either metal or plastic. A rigid, biocompatible plastic such as polyurethane is preferred, and is indicated as the material in FIG. 1.

The pressure transducer 14 is of the fiber optic type which converts sensed pressure variations into a light modulated signal. The device is calibrated so that the light signal is proportional to pressure. Fiber optic leads or paths are the preferred mode of light transmission from a light source. Such leads may be in the configuration of a single fiber bundle which serves to both send and receive light signals to and from the transducer, or in the form of two fiber optic leads. The dual lead configuration is preferred and is disclosed herein, reference numerals 24 and 26 indicating a pair of elongated, parallel fiber optic leads which extend longitudinally within the tubular passage defined by guide wire 12. It is to be noted that guide wire 12 is of a very small diameter on the order of 0.038 inches in outer diameter, and 0.028 inches on its inner diameter. The distal ends of fiber optic leads 24 and 26 terminate within connector block 16, and their proximal end portions 24aa and 26a terminate within the pressure transducer assembly 14. Connector 16 serves to connect the transducer leads to a control unit which provides a signal output display and a light-generating source. Lead 24 serves as a light signal transmitting path for transmitting light from the light source to the pressure transducer 14. Fiber optic lead 26 serves to convey light signals from the transducer back to the control unit (not shown) from connector block 16. The proximal end portion 24aa of lead 24 includes a terminal end segment 24a and a separate, proximal end segment 28 which terminates at its proximal end 28a and serves as part of the light transmitting path in combination with the remainder of lead or path 24. Lead or fiber optic path 24 thus has a proximal end portion defining a proximal end including terminal end segment 24a of lead 24 and proximal end segment 28 having a proximal end 28a. Fiber optic leads and lead segments 24, 24a, 28, and 26 comprise a light-transmitting circuit.

The transducer assembly 14 includes a housing 30 which is wholly contained within guide wire 12 near the proximal end thereof. Housing 30 may be made from metal or plastic. Biocompatible, rigid plastic, such as polyurethane, is preferred. Alternatively, housing 30 could be made of stainless steel. Housing 30 is shown most clearly in the perspective view of FIG. 3. It is preferably of cylindrical shape, and has opposed end faces 30a and 30b. Parallel, elongated tubular passages 32 and 36 are formed within housing 30 for receiving the proximal end portions of fiber optic leads 24 and 26 in the manner shown in FIG. 1. The end of housing 30 adjacent to end face 30b is hollow or open as shown in FIG. 1 to provide a cavity 38 within which light signals may be transmitted between the proximal end portion of the first and second fiber optic leads 24 and 26. For that purpose, in the preferred embodiment as disclosed herein, a reflector 40 is utilized. Reflector 40 comprises a concave surface which may be either formed on or applied to the inner end of end cap 22. As stated above, end cap 22 may be made out of metal or plastic. Preferably, end cap 22 is formed to provide a concave recess on its inner end which forms a segment of a sphere. If end cap 22 is made out of plastic, preferably relatively hard, biocompatible polyurethane as shown, reflector surface 40 will comprise a metal surface electroplated thereon, or a hot stamped, reflective coating applied to the inner end of end cap 22. If end cap 22 is made of metal, such as titanium or stainless steel, reflector surface 40 will simply comprise a polished, concave surface on the inner end of cap 22.

As also appears most clearly in FIG. 3, housing 30 is molded or cut out to the configuration shown so as to provide a central recess or cavity defined by opposed end faces 42 and 43 and flat surface 44 extending therebetween. The portion of cylindrical housing 30 extending between cavity face 43 and end face 30b of the housing includes a further, elongated tubular passage 34 within which proximal end segment 28 of lead 24 is received and contained. It is to be noted that the proximal end segment 24a and proximal end portion 26a of leads 24 and 26, as well as proximal end segment 28 and its proximal end 28a are held and maintained in the orientation shown in FIG. 3 within housing 30 in order that the light may be properly transmitted through the transducer assembly.

The aforesaid cavity or recess formed in housing 30 between faces 42 and 43 defines a gap across which the terminal end segment 24a of lead 24 and its aligned, proximal end segment 28 are separated. Terminal end segment 24a of fiber optic lead 24 is on one side of the gap, and proximal end segment 28 of the light-sending lead 24 is on the opposite side of the gap in light-receiving juxtaposition to the terminal end segment 24a.

An opening is cut in the coils of guide wire 12 in a configuration conforming to the outer perimeter of the cavity or recess formed in housing 30 between its end faces 42 and 43 and bottom wall 44. That opening in the guide wire coil serves as an aperture or port for pressure sensing. Preferably, the coils of guide wire 12 are joined together along a portion of the length thereof around the aforesaid opening in the area of pressure transducer 14 to provide increased rigidity and a unitary structure along that portion of the length of the guide wire on and within which the pressure transducer is mounted. The coils of the guide wire may be joined together in various ways, as by brazing, soldering, or fusing. Silver soldering has proven to be an effective technique for that purpose, and reference numeral 45 in FIG. 1 indicates the solder material joining coils of the guide wire together in the area of the pressure transducer 14.

For the purpose of sensing changes in pressure, a flexible membrane 46 is positioned on the guide wire. Flexible membrane 46 is disposed in covering relation to the guide wire opening, adjacent to and opposite the gap between terminal end segment 24a and proximal end segment 28 of fiber optic lead 24. The portion 48 of flexible membrane 46 which overlies the opening in the guide wire coil is a pressure-sensitive segment which is free to flex or deflect transversely with respect to the path of light passing longitudinally between aligned terminal end segment 24a and proximal end segment 28 of fiber optic lead 24. Membrane 46 may take the form of a patch or a sleeve. Preferably, as may be noted most clearly by reference to FIG. 2, membrane 46 is in the form of a cylindrical sleeve embracing the guide wire in a snug fit therewith. The material of the membrane sleeve is preferably elastomeric, and could be urethane or silicone. Silicone has been found to be preferable, and also meets the need of a biocompatible material which is bondable to the biocompatible coating 20 on the outside of coil 12 to provide a leak-free seal at the juncture points therewith as shown in FIG. 1.

As a particularly beneficial feature, flexible membrane 46 is secured around the outside of guide wire 12 over the window opening cut therein so as to be placed in tension in a prestressed condition. For that purpose, membrane sleeve 48 has an outside diameter of 0.027 inches relative to the preferred inside diameter of 0.028 inches for guide wire coil 12. Membrane sleeve 46 is stretched so as to get it over guide wire coil 12. Alternatively, silicone membrane sleeve 46 may be placed in a solution which causes it to expand, after which it is slipped over the end of the guide wire coil in covering relation to the window or opening. The membrane sleeve then shrinks as it dries. In either case, the membrane sleeve 46 is prestressed in tension around guide wire coil 12 and over the opening. This causes the membrane to be initially set at an inwardly flexed condition in which pressure responsive segment 48 thereof is curved inwardly. As shown in FIGS. 1 and 2, pressure responsive segment 48 assumes the shape of a segment of a sphere in its inwardly curved set position. The membrane sleeve is placed in tension a predetermined extent so that segment 48 will have an inward, initial deflection of approximately 0.005 inches. This is sufficient inward deflection that segment 48 will extend slightly into the linear path of light traveling between terminal end segment 24a of fiber optic lead 24 and separate, proximal end segment 28 thereof. Segment 48 is free to flex either inwardly or outwardly. Thus, because of its initial, inward deflection partially blocking the flow of light through the fiber optic, light-transmitting circuit, it is able to sense negative pressures or pressure decreases within the body of a patient. Thus, if the pressure being sensed externally of pressure transducer 14 on the outer surface of membrane segment 48 decreases, the membrane will flex slightly outwardly to permit a greater passage of light through the gap between terminal end segment 24a and proximal end segment 28 of the first fiber optic path. This change in light transmission will be sensed as a signal indicating a decrease or negative change in pressure.

The deflection of membrane segment 48 in response to changes in the pressure differential across its inner and outer faces is assured by connecting the underside or inner face of membrane segment 48 to atmospheric pressure. For this purpose, slots 50 and 52 are cut along the length of housing 30 so as to communicate with the underside of membrane segment 48, through the central recess in housing 30, as shown in FIG. 3. Slots 50 and 52 communicate through the open, inner passageway define inside of sealed guide wire 12 with a final passage 54 formed in connector block 16. Passage 54 communicates with atmospheric pressure so that atmospheric pressure will be conducted to the underside or inside face of membrane segment 48.

As shown in FIG. 1, reflector 40 is spaced apart from proximal end portions of the two fiber optic paths 24 and 26, in opposing relation thereto. Thus, light signals conducted by terminal end segment 24a fiber optic lead 24 across the gap to fiber optic proximal end segment 28 are directed from proximal end segment 28a onto the surface of reflector 40, and are reflected back to proximal end portion 26a of fiber optic return path 26. Arrows within cavity 38 of housing 30 indicate such light transmission to and from reflector 40. The distance between fiber optic proximal end portions and the surface of reflector 40 is predetermined so as to control the focal length of reflector 40 and thus to optimize light signal transmission.

Utilizing separate fiber optic proximal end segment 28 in alignment with terminal end segment 24a of fiber optic lead 24, and providing the light transmission control gap therebetween, provides particular benefits. Light signals transmitted from lead proximal end segment 24a of 24 across the gap to proximal end segment 28 are partially obstructed and interrupted by the deflection of pressure-responsive segment 48 of membrane 46. However, all of the light which passes across the gap to proximal end segment 28 is fully directed from end 28a thereof to reflector 40 without obstruction. Thus, much greater light reflection resolution onto proximal end portion 26a of fiber optic return path or lead 26 is achieved than would be the case if reflector 40 were positioned directly across the membrane gap from proximal end segment 24a of lead 24, without using additional, proximal end segment 28.

The operation of the pressure transducer is believed to be clearly understood from the foregoing description. The outer surface of pressure-responsive segment 48 of membrane 46 exterior of housing 30 is exposed to pressure within the body of a patient. The inner surface of membrane segment 48 is exposed to pressure inside of housing 30, which will normally be atmospheric pressure as provided through slots 50 and 52 and passage 54 in connector block 16. Thus, any pressure increase within a patient's body as sensed on the outside surface of pressure-responsive segment 48 of membrane 46 will cause segment 48 to deflect inwardly into the gap provided between terminal end segment 24a of fiber optic lead 24 and the adjacent end of lead proximal end segment 28. The passage of light across the gap between end wall faces 42 and 43 of housing 30 will thus be more obstructed or restricted, and this change in light transmission will be reflected to lead 26 as a return signal indicative of an increase in pressure within a patient's body. Any decrease in pressure within the patient's body as sensed on the outside surface of membrane segment 48 will cause that membrane to deflect more outwardly, and thus permit more light to pass across the gap to lead proximal end segment 28. A return signal to fiber optic lead 26 indicative of a pressure decrease will thus be transmitted.

The guide wire and pressure transducer assembly disclosed herein may be used in various applications for invasive monitoring of fluid and gas pressures in patients in hospital operating rooms and intensive care units. The fluid monitoring category includes arterial and central venous blood pressures, cerebral spinal fluid, and intracranial pressures, intrauterine pressures, and urodynamic measurements.

It is anticipated that various changes can be made in the size, shape, and construction of the fiber optic pressure transducer and guide wire assembly disclosed herein without departing from the spirit and scope of the invention as defined by the following claims:

What is claimed is:

1. A transvenously-insertable guide wire and physiological pressure transducer assembly comprising:

an elongated guide wire comprised of multiple coils of wire defining an elongated tubular passage, said guide wire being sufficiently flexible to traverse a patient's vascular system and having a proximal end and a distal end;

first and second fiber optic paths extending longitudinally within said tubular passage of said guide wire and defining a light transmitting circuit, said first fiber optic path adapted to be a light transmitter for transmitting light from an external source and said second fiber optic path adapted to be a transmitter for returning light signals, each of said fiber optic paths having a proximal end portion and a distal end; and a pressure transducer mounted on said guide wire at the proximal end portions of said fiber optic paths, said transducer comprising;

a housing wholly contained and restrained within said guide wire between said proximal and distal ends thereof and receiving and holding said proximal end portions of said fiber optic paths in predetermined positions for light transmission therethrough;

a gap in said proximal end portions of said fiber optic paths of the light transmitting circuit within said housing through which light passes;

an opening in the side of said guide wire adjacent to said gap and said housing and in fluidic communication with said gap; and a flexible membrane on said guide wire disposed in covering relation to said opening, said membrane having a pressure responsive segment extending over said opening and exposed to pressure exterior of said housing on its outer surface and to pressure inside of said housing on its inner surface, said pressure responsive segment of said membrane being movable transversely across said gap in response to changes in pressure exterior of said housing to change light transmission through said proximal end portions of said fiber optic paths.

2. The guide wire and pressure transducer assembly of claim 1 wherein: the coils of said guide wire are joined together in the area of said pressure transducer to provide a unitary structure along a portion of the length of said guide wire.

3. The guide wire and pressure transducer assembly of claim 2 wherein:

the coils of said guide wire are joined together along said portion of the length thereof by silver soldering.

4. The guide wire and pressure transducer assembly of claim 2 wherein:

said housing is of generally cylindrical shape and is contained within said portion of the length of said guide wire along which the coils of said guide wire are joined together.

5. The guide wire and pressure transducer assembly of claim 1 wherein:

the inner surface of said pressure responsive segment of said membrane is exposed to atmospheric pressure by passage means extending through said guide wire.

6. The guide wire and pressure transducer assembly of claim 5 wherein:

said passage means includes at least one elongated passage formed in said housing and communicating with the inner surface of said pressure responsive segment of said membrane.

7. The guide wire and pressure transducer assembly of claim 1 wherein:
said membrane is a cylindrical sleeve embracing said guide wire in a snug fit therewith.

8. The guide wire and pressure transducer assembly of claim 7 wherein:
said membrane sleeve is of elastomeric material and is stretched over said opening in the guide wire so as to be in tension with said pressure responsive segment thereof being deflected through said opening into said gap, whereby said pressure responsive segment will deflect outwardly in response to a decrease in pressure exterior of said housing and thus present less of an obstruction to light transmission across said gap.

9. The guide wire and pressure transducer assembly of claim 1 wherein:
said proximal end portions of said first and second fiber optic paths are optically coupled to each other by means of a reflector spaced apart from said proximal end portions of said fiber optic paths a predetermined distance in opposing relation thereto, whereby light signals from the proximal end portion of said first fiber optic path will be reflected back to the proximal end portion of said second fiber optic path.

10. The guide wire and pressure transducer assembly of claim 9 wherein:
the proximal end portion of said first fiber optic path is comprised of a terminal end segment thereof defining one side of said gap and a separate, spaced apart and aligned proximal end segment thereof defining the opposite side of said gap in light receiving juxtaposition to said terminal end segment, whereby movement of said flexible membrane changes light transmission across said gap between said terminal end segment and said proximal end segment of said first fiber optic path.

11. The guide wire and pressure transducer assembly of claim 10 wherein:
said reflector is spaced apart from said proximal end segment of said first fiber optic path and said proximal end portion of said second fiber optic path for reflecting light from said proximal end segment to said proximal end portion of said second fiber optic path.

12. The guide wire and pressure transducer assembly of claim 11 wherein:
said proximal end of said guide wire is closed by an end cap, and said reflector comprises a reflective surface on the inner end of said end cap inside of said guide wire.

13. The guide wire and pressure transducer assembly of claim 12 wherein:
said reflective surface is concave.

14. The guide wire and pressure transducer assembly of claim 12 wherein:
said end cap is made of metal and said reflective surface comprises a polished surface on the inner end thereof.

15. A transvenously-insertable guide wire and physiological pressure transducer assembly comprising:
an elongated guide wire comprised of multiple coils of wire defining an elongated tubular passage, said guide wire having a proximal end and a distal end;
fiber optic path means extending longitudinally within said tubular passage of said guide wire and defining a light transmitting circuit, said fiber optic path means having proximal end portions and a distal end; and
a pressure transducer mounted on said guide wire at the proximal end portions of said fiber optic path means, said transducer comprising;
a housing wholly contained and restrained within said guide wire between said proximal and distal ends thereof and receiving and holding said proximal end portions of said fiber optic path means in a predetermined position;
a gap in said proximal end portions of said fiber optic path means of the light transmitting circuit within said housing through which light passes;
an opening in said guide wire adjacent to said gap and said housing and in fluidic communication with said gap, and the coils of said guide wire being joined together in the area of said pressure transducer for increased strength and rigidity along a portion of the length of said guide wire; and
a flexible membrane on said guide wire disposed in covering relation to said opening, said membrane having a pressure-responsive segment extending over said opening and exposed to pressure exterior of said housing on its outer surface and to pressure inside of said housing on its inner surface, said pressure-responsive segment of said membrane being movable across said gap in response to changes in pressure exterior of said housing to change light transmission through said proximal end portions of said fiber optic path means.

16. The guide wire and pressure transducer assembly of claim 15 wherein:
said fiber optic path means comprises a first fiber optic path adapted to be a light transmitter for transmitting light signals from an external source to the pressure transducer and a second fiber optic path adapted to return light signals received from said transducer, each of said fiber optic paths having a proximal end portion and a distal end, with their proximal end portions being received and held within said housing.

17. The guide wire and pressure transducer assembly of claim 16 wherein:
said housing has a cavity formed therein between opposing wall faces, said gap being defined between said wall faces.

18. The guide wire and pressure transducer assembly of claim 15 wherein:
the coils of said guide wire are joined together along said portion of the length thereof by silver soldering 19. The guide wire and pressure transducer assembly of claim 15 wherein:
said housing is of generally cylindrical shape and is contained within said portion of the length of said guide wire along which the coils of said guide wire are joined together 20. The guide wire and pressure transducer assembly of claim 15 wherein:
said flexible membrane is stretched over the outside of said guide wire in covering relation to said opening so as to be in tension with said pressure-responsive segment thereof being deflected through said opening into said gap in partially obstructing relation to the transmission of light across said gap, whereby said pressure responsive segment will deflect outwardly in response to a decrease in pressure exterior of said housing and thus present less of an obstruction to light transmission across said gap.

* * * * *